United States Patent
Rao et al.

[11] Patent Number: 5,919,136
[45] Date of Patent: Jul. 6, 1999

[54] APPARATUS FOR THE STUDY OF ANORECTAL FUNCTION

[75] Inventors: Satish Sanku Chander Rao, Iowa City, Iowa; Joel Klaus Quaid, Santa Barbara, Calif.

[73] Assignees: BioEnterics Corporation, Carpinteria, Calif.; University of Iowa Research Fnd, Iowa City, Iowa

[21] Appl. No.: 08/650,036

[22] Filed: May 17, 1996

[51] Int. Cl.$^6$ ....................................................... A61B 6/00
[52] U.S. Cl. ............................................ 600/431; 600/587
[58] Field of Search ..................................... 128/630, 654, 128/774, 899, DIG. 25; 600/29–32, 300, 431, 587; 623/8; 606/192, 197

[56] References Cited

U.S. PATENT DOCUMENTS

| | | | |
|---|---|---|---|
| 4,253,201 | 3/1981 | Ross et al. | 623/8 |
| 4,624,671 | 11/1986 | Kress | 623/8 |
| 4,650,487 | 3/1987 | Chaglassian | 623/8 |
| 4,687,002 | 8/1987 | Lahr | 128/774 |

*Primary Examiner*—Ruth S. Smith
*Attorney, Agent, or Firm*—Michael G. Petit

[57] ABSTRACT

A device for evaluating anorectal function. The device is a silicone gel-filled deformable artificial stool adapted for transanal insertion within the rectum and having an adjustable volume, and a shape consistency and size similar to a normal stool. The device has an elongate extensible silicone elastomer outer shell overlying and affixed to a coaxially mounted inflatable inner shell to create a sealed cylindrical space between the outer and inner shells. The elastic outer shell preferably incorporates a radiopaque material homogeneously dispersed within the silicon elastomer, alternatively, inner balloon affixed thereto. Radiopaque fluid is introduced into the cylindrical space to provide a means for radiographically observing the in situ deformation of the device when placed within the rectum of a subject. One end of a flexible fill tube projects within the volume enclosed and defined by the inflatable inner shell and is affixed thereto. The opposing free end of the fill tube (tail) extends away from the inner tube. A lumen within the fill tube provides leak-proof fluid communication between the interior of the inner shell and the free end of the fill tube. The free end of the fill tube includes a self-sealing valve inserted within and plugging the lumen providing a means through which a fluid or air may be injected into, or withdrawn from, the inner shell to adjust the volume of the device in situ. The free end of the fill tube may also be used for withdrawing the device from the rectum. The device has a shape and consistency of a stool and further includes means for adjusting the volume of the device in vivo to evoke an optimal sensation of stooling.

10 Claims, 1 Drawing Sheet

APPARATUS FOR THE STUDY OF ANORECTAL FUNCTION

BACKGROUND OF THE INVENTION

1. Field of the Invention

A device adapted for insertion into the rectum for artificially simulating a stool therewithin and a method for using the device for evaluating anorectal function.

2. Prior Art

Disorders of defecation affect 10% of the population. Constipation in adults and encopresis in children account for a majority of these disorders. A device placed within the rectum of a patient can be used to provide information necessary for making a clinical evaluation of such disorders. Such a device enables the clinician to confirm a diagnosis of obstructive defecation and generally screen patients complaining of constipation for this disorder.

Prior art devices used for evaluating anorectal function include various water filled balloons and a more or less cohesive mass formed from an intimate mixture of mashed potatoes and barium sulfate. A device such as a water-filled balloon is inserted in the patient's rectum and inflated to simulate a stool. The time required for expelling the device from the rectum provides a measure of the person's ability to eliminate stool. A mixture of mashed potatoes and barium sulfate provides a somewhat cohesive malleable mass, having a consistency similar to a stool and which, when contained within the rectum, is deformed during defecation enabling the changes to be followed by radiography. A disadvantage of the water-filled balloon is that there is no means for following the progression of deformation during defection by radiography. Further, such water-filled balloons generally do not have the consistency and rheologic properties of an actual stool. The cohesive mass formed from mixing barium sulfate with mashed potatoes lacks the structural integrity of an actual stool, requires a caulking gun and unusual force to inject into the rectum, is messy and generally not acceptable to either radiologists or patients. Thus, the prior art devices have deficiencies which have not been overcome.

SUMMARY OF THE INVENTION

The present invention is an artificial stool adapted for insertion into the rectum and a method for employing the device for evaluating a person's ability to defecate. The device simulates a stool; having a consistency and shape approximating an actual stool. The device consists of an elongate cylindrical member having an extendible elastomeric outer shell overlying an inflatable elastomeric inner shell and sealingly affixed thereto. A cylindrical space between the inflatable inner shell and the extensible outer shell is filled with a viscous fluid such as silicone gel having a viscosity permitting deformation of the device. The viscous fluid may contain a radiopaque component homogeneously distributed in the viscous fluid in a concentration which permits in situ radiographic observation of the device during expulsion from the rectum. More preferably, the radiopaque component is incorporated into the elastomeric outer shell during production. A fill tube having a central lumen has a free end in fluid communication with the interior of the inner shell and extending therefrom to terminate in a free end which includes a selfsealing fill port plugging the lumen. The outer shell is torpedo-shaped to facilitate insertion into a subject's rectum. Following transanal insertion into the rectum, the device may be inflated or deflated in situ to adjust the volume thereby optimizing the perception by the host subject of an actual stool present within the rectum. The shape and movement of the device which occurs during the subject's defecation effort to expel the device from the rectum may be observed by radiography.

It is an object of the present invention to provide an artificial stool adapted for insertion into a person's rectum and having a shape and consistency which provide a sensation within the person similar to the sensation presented by the presence of a stool.

It is another object of this invention to provide a device for evaluating anorectal function.

It is still another object of this invention to provide a device which may be painlessly inserted into the rectum and the size of the device adjusted following insertion to produce a sensation of stooling in a subject.

It is another object of this invention to provide the device meeting the above objectives and further providing a method for using the device for evaluating anal-rectal function for studying.

The features of the invention believed to be novel are set forth with particularity in the appended claims. However, the invention itself, both as to organization and method of operation, together with further objects and advantages thereof may best be understood by reference to the following description taken in conjunction with the accompanying drawings in which:

DESCRIPTION OF THE PREFERRED EMBODIMENTS

Figure 1:
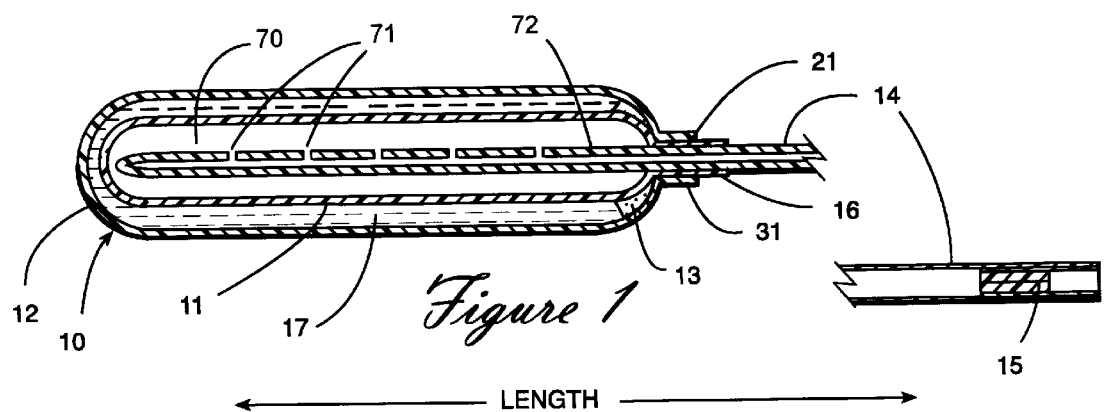
FIG. 1 is an elevational cross sectional view of an embodiment of the device in accordance with the present invention.

A cross sectional elevational view of a device perceptibly simulating a stool when disposed within a person's rectum in accordance with the present invention is shown at 10 in FIG. 1. The device 10 has an inner shell 11 comprising an elongate inflatable elastomeric balloon having an elongate, cylindrical neck 21 projecting therefrom with an opening in the terminal end thereof. The inner shell 11 is enclosed by an axially mounted elongate elastomeric outer shell 12. The outer shell 12 has a circular opening in the end thereof which is affixed to outer surface of the neck portion 21 of the inner shell 11 by an adhesive 13. A portion 16 of the elongate cylindrical neck portion 21 of the inner shell projects proximally from within the outer shell 12. One end of the fill tube 14 is inserted through the neck portion 21 and disposed within the inner shell 11. The fill tube 14 extends through the neck portion 21 of the inner shell 11 and is affixed to the neck portion by means of an adhesive. A valve 15 disposed within the central axial lumen of the fill tube 14 near the free end of the fill tube occludes the lumen and provides sealable fluid flow access to the lumen with the fill tube which is in fluid communication with the interior volume defined by the inner shell 11.

Figure 2:
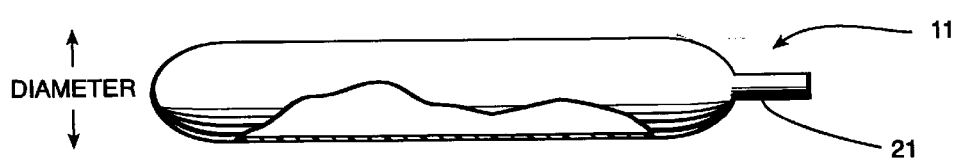
FIG. 2 is a partially cut away perspective view of the inner shell of the device in accordance with the present invention.

A device 10 in accordance with the present invention may be assembled from pre-assembled components. The inner shell 11 is shown in FIG. 2. The inner shell 11 is made by repeatedly dipping an inner shell-shaped mandrel mounted upon a dipping rod into a suitable elastomer dispersion such as silicone dispersion. The length of the inner shell mandrel is approximately 4–5 inches overall with the elongate neck portion 21 being about 1 inch long. The diameter of the inner mandrel is approximately 0.25–0.5 inches with 0.36 inches being a suitable diameter. The mandrel is repeatedly dipped into a silicone dispersion until the wall thickness is approximately 0.020 inches. Xylene can be used to control the viscosity of the dispersion when using silicone as the elastomer to provide a uniform film over the mandrel when the mandrel is removed from the fluid dispersion. A drying period between dips of approximately 45 minutes allows the xylene to evaporate prior to re-dipping the mandrel. After the coating of elastomer on the surface of the mandrel has built up to the desired thickness, the elastomer-coated mandrel is placed in an oven and the elastomer coating vulcanized at approximately 300° Fahrenheit for 1.5 hours. The inner shell is removed from the mandrel by cutting the coating around the terminus of the neck portion and removing the inner shell from the mandrel by everting the shell and peeling it off. In some instances it might be necessary to dip the coated mandrel in xylene to swell the shell in order to facilitate removal of the shell from the mandrel.

Figure 3:
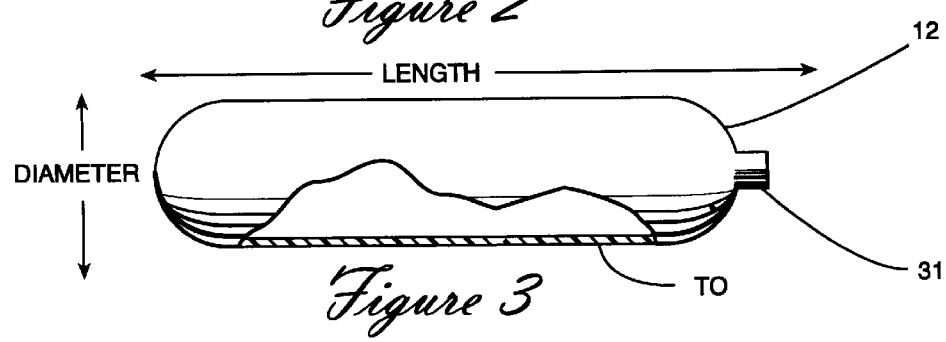
FIG. 3 shows the construction of the outer shell of the device in accordance with the present invention.

The outer shell 12, shown in FIG. 3, is made in a similar manner to the inner shell 11 except that the mandrel used to cast the shell is dimensioned to provide a mandrel outer surface having the approximate dimensions of the outer shell set forth in FIG. 3. The overall length of the outer shell 12 is approximately 4 inches and the outer diameter is approximately 0.75–1 inch with a preferred diameter of about 0.84 inches. The outer shell thickness is approximately 0.020 inches. The proximal end 31 of the outer shell 12 is cut in order to remove the shell from the mandrel and provide a circular aperture in the shell dimensioned to permit the inner shell to be inserted therethrough.

Figure 4:
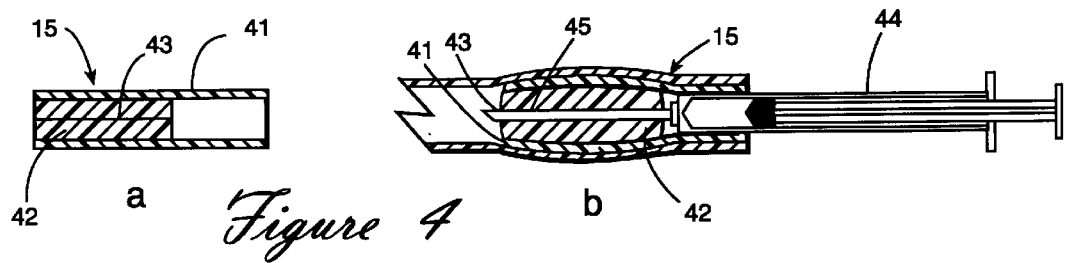
FIG. 4(a) is a detail cross-sectional view of a fill valve sub-assembly for use with the device.
FIG. 4(b) showing the fill valve inserted within the lumen of the fill tube at the free end and a syringe needle passing therethrough for adjusting the volume of the device.

A self-sealing valve 15, shown in elevational cross section in FIG. 4(*a*), is made for insertion within the fill tube lumen as follows. A section of silicone tubing 41 approximately 0.5 inches long and having an inner (lumen) diameter of approximately 0.104 inches and an outer diameter of about 0.192 inches is presented. A silicone adhesive 42 is injected into the lumen within the tube to fill about one half of the length of the lumen (0.25 inches). The adhesive is cured which takes roughly 24 hours at room temperature. Using a razor blade, the adhesive-filled end of the tubing and the silicone plug contained within the lumen thereof is slit lengthwise, the slit 43 extending approximately 1/64 inch past the plug formed from the cured adhesive filler 42. The fill valve 15 is then inserted with the lumen of the fill tube 14 adjacent to the free end thereof After the above subcomponents of the assembly are made, the device 10 is assembled as follows. A fill tube 14 comprising silicone tubing having an inner diameter of approximately 0.104 inches and an outer diameter of approximately 0.192 inches is cut into a 9 inch length. The proximal end of the tubing 14 is swelled by soaking in xylene. Once the inner diameter of the tubing has increased sufficiently, the self-sealing valve 15 is inserted into the lumen, plug end first and advanced until the valve is completely within the fill tube lumen. Upon drying the xylene evaporates and the wall of the fill tube 14 will retract around the fill valve 15 compressing the slit plug thereby providing a valve sealable to the tract of a needle or similar device passed therethrough.

Figure 5:
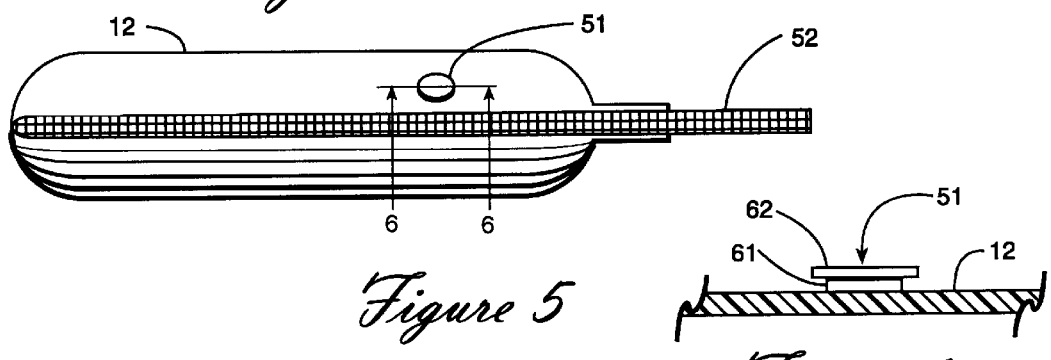
FIG. 5 is an elevational view of the outer shell in accordance with FIG. 2 showing a reinforced fill button and reinforcing straps affixed thereto.
Figure 6:
FIG. 6 is cross-sectional detail through view lines 6—6 of FIG. 5.

Both the inner and the outer shells should be washed in alcohol prior to assembly. As shown in FIGS. 5 and 6, a fill button 51 providing reinforcing means 51 for injecting a fluid such as a gel into the space defined between the inner and the outer shells may be formed and vulcanized onto the outer shell prior to assembly as follows. A disk of uncured silicone sheeting 61 approximately 4 mm in diameter is cut and placed against the wall 12 of the outer shell as shown in FIGS. 5 and 6. A second disk 62 having a diameter of approximately 6 mm of vulcanized 0.010 silicone sheeting is then placed over the 4 mm unvulcanized disk 61. The outer shell with the discs 61 and 62 in position is vulcanized to affix the fill button to the outer shell by heating to 300° F. for 3 minutes at 20 PSI. After the fill button 51 is affixed to the wall of the outer shell, the distal end of fill tube 14 is inserted within the inner shell and the outer surface of the fill tube adjacent to the neck portion of the inner tube is affixed thereto by means of silicone adhesive. The inner shell, including the tubing affixed thereto, is inserted into the opening in the outer shell and affixed thereto by means of silicone adhesive as discussed previously with regard to the inner shell. Elongate reinforcing straps 52 may be vulcanized or otherwise affixed to the outer surface of the outer shell to extend beyond the open end 31 of the outer shell so as to overlie the neck portion of the inner shell and a portion of the fill tube 14. The straps 52 are then affixed to the outer surface of the neck portion 21 and fill tube 14 by adhesive means and the device 10 finally dipped in an elastomer dispersion to form a uniform coating of elastomer over the assembly. The strap or straps 52 can be made from dacron mesh and securely affix the fill tube and the inner shell to the outer shell. The reinforcing straps 52 should project beyond the open end of the outer shell approximately 5 cm to provide sufficient overlap for the straps to be vulcanized or otherwise affixed to the projecting neck portion of the inner shell and the fill tube.

Using a syringe (not shown), a silicone gel adhesive 13 is injected into the proximal portion of the space defined between the inner and the outer shells through the fill button 51 in the outer shell to provide a leak-proof seal therebetween. After the adhesive 13 has dried, the portion of the device 10 comprising the junction between the outer shell and the inner shell and the fill tube is preferably dip coated in a silicone dispersion and finally dried and cured in a preheated oven for one hour at approximately 300° F. A hypodermic needle 45 mounted on a syringe 44 may be used to introduce the adhesive 13, a gel 17 and/or a radiopaque material, such as barium sulfate, into the volume defined between the inner and the outer shells. The inner shell may be inflated with a fluid such as air or water to adjust the volume of the device as shown in FIG. 4(*b*) which will enter the cavity 70 in the inner shell 11 through apertures 71 formed in the proximal region 72 of the fill tube 14. A gel 17 useful for filling the space between the inner and the outer shells can be made by adding 50 grams of a crosslinker to 120 grams of a silicone gel. An 18 gauge needle 45 affixed to an injection syringe 44 filled with a suitable gel may be inserted through the fill button and the gel injected into the space. The filled weight of the device following injection of the gel should be approximately 44 grams. The fill hole remaining in the fill button following withdrawal of the needle is sealed with a dip coat of elastomer dispersion and dried.

EXAMPLE

A test of simulated defecation is useful in evaluation of patient's with constipation or encopresis. Whether this test is influenced by the position, the presence of artificial stool in the form or consistency of stool is not known. In order to evaluate the effacy of the present device in determining these factors and to devising more optimal method for performing this test, the following examples show the test.

Twenty-five healthy volunteers, male/female ration equal to 10/15, having an average age of 50 years and ranging in age from 33 to 71 years, were selected for the study. The subjects were asked to strain, as if to defecate under four conditions:

1) with a multisensor soft state probe in the colon;
2) after rectal distention with a latex balloon containing 60 CC of air;
3) after placing a balloon in the rectum with 50 CC of water;
4) after placing a device in accordance with the present invention consisting of a cylindrical 9 mm long silicone-filled deformable device in the rectum.

Either a balloon or the present device was placed randomly in the subjects and the subjects were blinded. Tests were performed in two positions—lying in the left lateral end, sitting on a commode. During conditions 1 and 2, rectal and anal impressions were analyzed. During 3 and 4, the time taken to expel each device was measured and subjective response was assessed on a visual analog scale. During condition 1, in the lying position, a pattern of obstructive defecation was seen in 10/25 (40%) of the subjects and during condition 2 in 10/25 (40%) in the subjects. In contrast, on the commode, during both conditions, only 2/25 (8%) of the subjects showed this pattern. In the lying position, 15/25 (60%) of the subjects could no expel the 50 CC balloon and 11/25 (44%) of the subjects could not expel the present device. In contrast, on the commode, 4 subjects failed to expel the balloon and 2 the present device. Mean time for expelling the device was lower than the mean time for the balloon (45 seconds for the present device as opposed to 49 seconds for the balloon). 19 out of 25 subjects preferred the present device while 5 out of 25 preferred the balloon and one subject had no preference. Mean scores for the ability of the device to evoke a desire to defecate were 7 for the present device versus 5 for the balloon. Irrespective of rectal distention, when straining the rectal pressure and anal residual pressure was lower on the commode than on the bed. In conclusion, the device in accordance with the present invention simulates a stool when inserted within the rectum of a person and is a suitable device for evaluating anorectal function.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What we claim is:

1. A device for simulating a stool, the device being adapted to be inserted within the rectum of a person, the device comprising:

(a) a fill tube having a proximal end and a distal end and a lumen therebetween;
   (b) a fill valve disposed within said lumen adjacent to said proximal end of said fill tube, said fill valve being self-sealing to the track of a hollow bore needle;
   (c) an inner shell comprising an elongate flexible inflatable balloon affixed in fluid-tight connection to said distal end of said fill tube, said inner shell enveloping said distal end of said fill tube and in fluid communication with said lumen; and
   (d) an outer shell coaxially disposed over and enveloping at least a portion of said inner shell and affixed thereto to define a fluid-tight chamber interposed between and abounded by said inner shell and said outer shell, the fluid-tight chamber being at least partially filled with a viscous fluid, said outer shell having a generally cylindrical shape with rounded ends to approximate a stool.

2. The device of claim 1 wherein the said outer shell comprises an elastomer having a radiopaque material incorporated therein.

3. The device in accordance with claim 1 where in the viscous fluid includes a radiopaque material.

4. The device in accordance with claim 1 wherein the outer shell further includes a reinforced portion on the surface thereof for introducing the viscous fluid into said chamber.

5. The device in accordance with claim 1, further including at least one reinforcing strap affixed to at least a portion of the outer shell and said fill tube.

6. The device in accordance with claim 1, further including a fill button provided on the outer shell through which the viscous fluid may be injected into the fluid-tight chamber interposed between and bounded by said inner shell and said outer shell.

7. A device for simulating a stool, the device being adapted to be inserted within the rectum of a person, the device comprising:

(a) a fill tube having a proximal end and a distal end and a lumen therebetween;
   (b) a fill valve disposed within said lumen adjacent to said proximal end of said fill tube, said fill valve being self-sealing to the track of a hollow bore needle;
   (c) an inner shell comprising an elongate flexible inflatable balloon affixed in fluid-tight connection to said distal end of said fill tube, said inner shell enveloping said distal end of said fill tube and in fluid communication with said lumen;
   (d) an outer shell coaxially disposed over and enveloping at least a portion of said inner shell and affixed thereto to define a fluid-tight chamber interposed between and abounded by said inner shell and said outer shell, said outer shell having a generally cylindrical shape with rounded ends to approximate the shape of a stool; and
   (e) a gel which at least partially fills said chamber between said outer shell and said inner shell.

8. The device of claim 7 wherein the said outer shell comprises an elastomer having a radiopaque material incorporated therein.

9. The device in accordance with claim 7 wherein the gel includes a radiopaque material.

10. The device in accordance with claim 7, further including at least one reinforcing strap affixed to at least a portion of the outer shell and said fill tube.

* * * * *